United States Patent [19]

Murphy et al.

[11] Patent Number: 5,376,362
[45] Date of Patent: Dec. 27, 1994

[54] ANTIPERSPIRANT-DEODORANT COSMETIC PRODUCTS

[75] Inventors: Richard T. Murphy, Belle Mead; M. Stephen LaJoie, Basking Ridge, both of N.J.

[73] Assignee: Church & Dwight Co., Inc., Princeton, N.J.

[21] Appl. No.: 53,836

[22] Filed: Apr. 27, 1993

Related U.S. Application Data

[63] Continuation-in-part of Ser. No. 986,916, Dec. 8, 1992, Pat. No. 5,354,553.

[51] Int. Cl.$^5$ .......................... A61K 7/34; A61K 7/38
[52] U.S. Cl. .......................................... 424/66; 424/68; 424/401; 424/484; 424/493; 424/496; 424/497; 424/498; 424/502; 424/719; 424/722
[58] Field of Search ............... 424/66, 68, 401, 488, 424/498, 493, 502, 719, 722, 484, 496, 497

[56] References Cited

U.S. PATENT DOCUMENTS

| | | | |
|---|---|---|---|
| 4,822,602 | 4/1989 | Sabatelli | 424/65 |
| 4,832,945 | 5/1923 | Osipow et al. | 424/65 |

FOREIGN PATENT DOCUMENTS 2837088  3/1979  Germany .

*Primary Examiner*—Raymond J. Henley, III
*Assistant Examiner*—Phyllis G. Spivack
*Attorney, Agent, or Firm*—Charles B. Barris

[57] ABSTRACT

This invention provides a homogeneous antiperspirant cosmetic stick or roll-on product containing a deodorant ingredient which consists of particles that contain multiple fine crystallites of a bicarbonate compound encapsulated with a hydrophilic polymer coating that lowers the relative density of the particles and improves the dimensional stability of the cosmetic product.

21 Claims, 1 Drawing Sheet

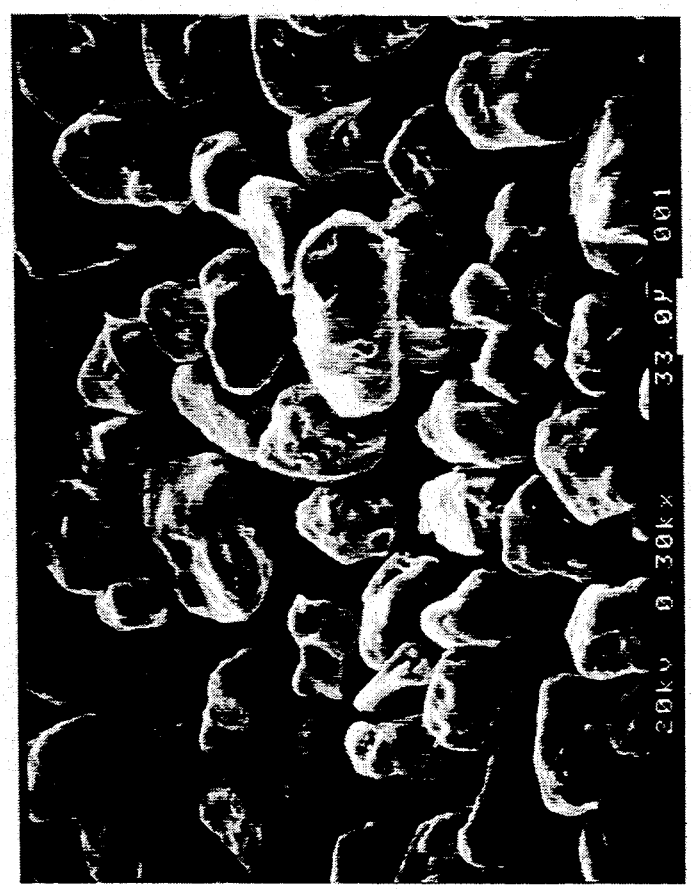
FIG. I

ANTIPERSPIRANT-DEODORANT COSMETIC PRODUCTS

CROSS-REFERENCE TO RELATED PATENT APPLICATION

This patent application is a continuation-in-part of patent application Ser. No. 07/986,916, filed Dec. 8, 1992, now U.S. Pat. No. 5,354,553, incorporated herein by reference.

BACKGROUND OF THE INVENTION

Antiperspirants combat axillary odors by inhibiting perspiration through the action of astringent salts such as aluminum and zinc salts, but may be irritating to a large number of users. Deodorants function by neutralizing the objectionable odors resulting from the degradation of several components of perspiration by chemical and microbial action into malodorous fatty acids.

Numerous solid antiperspirant and/or deodorant compositions have been described in the chemical and cosmetic literature. These compositions generally are emulsion sticks or suspensoid sticks. Emulsion sticks contain a solution of the antiperspirant ingredient incorporated into the stick via an emulsion. Although emulsion sticks are desirable in certain respects, they tend to be unstable, exhibit tackiness, and leave a visible residue on the skin after use. Suspensoid sticks contain the powdered antiperspirant ingredient suspended in the stick without the use of water or an emulsion. While suspensoids have stability, they tend to leave a white chalky residue on the skin after application.

Manufacturers have found that anhydrous antiperspirant stick systems are more marketable and have good consumer acceptance primarily due to the ease of application to the skin, good cosmetic esthetics and an acceptable degree of effectiveness. Previous to the development of anhydrous stick systems, numerous water based systems were developed in which the active astringent salts were solubilized in a thickened or gelled composition. This is exemplified in U.S. Pat. Nos. 2,732,327; 2,857,315; 3,255,082; and 3,928,557. The water based systems are difficult to apply to the skin, and their consistency and effectiveness are variable.

Many anhydrous stick compositions have been described in the literature which attempt to improve the delivery and the effectiveness of their antiperspirant and deodorant characteristics. Antiperspirant stick systems consisting of low molecular weight monohydric alcohols in conjunction with polyhydric alcohols are described in U.S. Pat. No. 4,137,306. These sticks have the advantage of quicker drying rates, but the residue of the polyhydric alcohols in combination with the astringent salts produces a high degree of tack, and their effectiveness is limited to the type and amount of astringent salts that could be incorporated in the stick matrix.

Anhydrous stick compositions that suspend the aluminum salt in a hydrophobic matrix are described in U.S. Pat. No. 4,049,792. These compositions employ waxy materials and long chain fatty esters to form a stick that delivers the active astringent salts to the skin. Cosmetic stick compositions made in accordance with these embodiments are greasy, and the active astringent salt is enveloped in a manner that prevents maximum performance. To alleviate this inherent negative characteristic, volatile silicone fluids replacement of the less volatile long chain fatty esters is described in U.S. Pat. No. 4,126,679. This disclosure teaches the advantage of utilizing a volatile non-staining liquid such as cyclic dimethylpolysiloxanes (referred to as volatile silicones), in combination with various types of waxes, as a carrier for the active astringent salts in an antiperspirant stick composition. Similar antiperspirant stick compositions containing volatile silicones are described in U.S. Pat. Nos. 4,511,554; 4,980,156; and 4,985,238.

With respect to deodorant activity, sodium bicarbonate has long been recognized for its deodorant properties, and has commonly been used as a household deodorant. Plain powdered sodium bicarbonate, or sodium bicarbonate diluted with talc or other filler, has been used as an underarm deodorant as disclosed in U.S. Pat. No. 4,382,079. Other publications which describe cosmetic stick compositions containing a bicarbonate deodorant include U.S. Pat. No. 4,822,602 and U.S. Pat. No. 4,832,945.

However, .the development of a practical and effective antiperspirant composition in cosmetic stick or roll-on form which is also capable of deodorization, and which is capable of consumer acceptability, presents many factors which are unique. Because alkali metal and ammonium bicarbonate have only limited solubility in water, alcohol and other solvents, the preparation of a composition suitable for dispensing in cosmetic stick or roll-on form has involved many processing obstacles. In addition to the problem of limited solubility, a bicarbonate ingredient is incompatible with the active astringent salts and with other ingredients of conventional stick compositions. Also, the dimensional stability of the cosmetic product containing bicarbonate ingredient, and the esthetic appearance and the "feel" on the skin, are just a few of the additional difficulties encountered in the preparation of a low residue antiperspirant-deodorant cosmetic product.

Another problem associated with the incorporation of a bicarbonate deodorant ingredient in an antiperspirant formulation is the tendency for the high density bicarbonate salt particles to settle in the fluid medium during processing. Also, under the elevated temperature conditions required for the admixing and blending of ingredients, bicarbonate degradation and evolution of carbon dioxide and water occur.

There is continuing interest in the development of antiperspirant cosmetic products which exhibit deodorizing activity, and in improved processes for their preparation.

Accordingly, it is an object of this invention to provide a process for the manufacture of an antiperspirant-deodorant cosmetic product which contains a bicarbonate deodorant ingredient, and which is characterized by excellent esthetics and cosmetic properties.

It is another object of this invention to provide a homogeneous antiperspirant cosmetic stick or roll-on product containing a compatible bicarbonate deodorant ingredient which is a particulate solid having particles with a hydrophilic polymeric coating that lowers the relative density of the particles, and improves the dimensional stability of the cosmetic product.

Other objects and advantages of the present invention shall become apparent from the accompanying description and examples.

DESCRIPTION OF THE INVENTION

One or more objects of the present invention are accomplished by the provision of a cosmetic stick product consisting of a solid organic matrix which contains about 0.5-20 weight percent of a particulate deodorant ingredient homogeneously dispersed therein, wherein the particles have an average particle size between about 5-60 microns, and an average dimensional axial ratio between about 1-2.5 to 1, and wherein the particles comprise a hydrophilic polymer surface coating having an encapsulated core content of at least two crystallites of water-soluble inorganic compound selected from alkali metal bicarbonate and ammonium bicarbonate.

In another embodiment this invention provides a cosmetic stick product consisting of a solid organic matrix comprising the following parts by weight of ingredients:

| | |
|---|---|
| volatile silicone oil | 10-55 |
| liquid emollient | 1-35 |
| low melting point wax | 12-30 | and the solid organic matrix has homogeneously dispersed therein about 0.5-20 parts by weight of a particulate deodorant ingredient which comprises particles having an average particle size between about 5-60 microns, and an average dimensional axial ratio between about 1-2.5 to 1, and wherein the particles comprise a hydrophilic polymer surface coating having an encapsulated core content of at least two crystallites of water-soluble inorganic compound selected from alkali metal bicarbonate and ammonium bicarbonate.

The term "particle size" as employed herein refers to the largest size dimension of a particle.

An invention cosmetic stick product can contain only a deodorant ingredient, or it also can include an antiperspirant ingredient. An invention antiperspirant-deodorant cosmetic stick product typically contains the following weight proportions of main ingredients:

| Ingredient | Weight |
|---|---|
| volatile silicone oil | 25-50 |
| liquid emollient | 2-20 |
| wax (MP 95°-180° F.) | 15-20 |
| antiperspirant | 20-28 |
| particulate bicarbonate deodorant | 0.1-25 |
| surfactant | 1-3 |

The volatile silicone oil ingredient in a cosmetic stick product of the present invention preferably is a cyclic or linear polydimethylsiloxane containing between about 3—9 silicon atoms. A suitable cyclic volatile polydimethylsiloxane compound is illustrated by the formula:

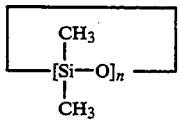

where n is an integer with a value of about 3-7.

A suitable linear polydimethylsiloxane is illustrated by the formula:

$(CH_3)_3Si-O[Si(CH_3)_2-O]_n-Si(CH_3)_3$ where n is an integer with a value of about 1-7.

Linear volatile silicone compounds generally have viscosities of less than about 5 centistokes at 25° C., while the cyclic type compounds have viscosities of less than about 10 centistokes.

Typical of the volatile silicone compounds that can be employed for purposes of the present invention is cyclomethicone, which is a cyclic dimethylpolysiloxane conforming to the above formula where n averages between 3-6. Dow Corning 245 Fluid (Dow Corning) is a cyclic volatile silicone which is commercially available. *CTFA Cosmetic Ingredient Dictionary*, Third Edition, (Estrin et al., Editors; The Cosmetic, Toiletry and Fragrance Association, Inc.; 1982) lists cyclic silicones on page 60, under the entry "Cyclomethicone".

The liquid emollient ingredient of an invention cosmetic stick product is selected from one or more water-insoluble organic compounds which are liquid at 25° C. and which contribute a combination of properties that are advantageous in an invention antiperspirant-deodorant cosmetic stick product.

The term "water-insoluble" as employed herein refers to an emollient ingredient which has a water-solubility of less than about one gram per 100 grams of water at 25° C.

A present invention emollient ingredient exhibits a low degree of irritation and toxicity in topical applications, and provides a softening or soothing effect on surface skin tissue.

Preferred water-insoluble liquid emollients include fatty acids such as oleic and ricinoleic; fatty alcohols such as oleyl, lauryl and hexadecyl; esters such as diisopropyl adipate, benzoic acid esters of $C_9$-$C_{15}$ alcohols, and isononyl isononanoate; alkanes such as mineral oil; silicones such as dimethylpolysiloxane and cyclic dimethylpolysiloxane; and ethers such as polyoxypropylene butyl ether and polyoxypropylene cetyl ether. Preferred water-insoluble liquid emollients include diisopropyl adipate, 2-ethylhexyl palmitate, dimethylpolysiloxane (50 cst.), and polyoxypropylene (14) butyl ether.

The low melting point wax ingredient of a present invention cosmetic stick product comprises one or more organic compounds which have a melting point in the range between about 95°-180° F.

Suitable types of wax-like compounds include fatty acids, fatty alcohols, fatty acid esters, fatty acid amides, and the like, which have an aliphatic chain length between about 8-30 carbon atoms. Illustrative of wax-like compounds are cetyl alcohol, palmitic acid, myristyl alcohol, stearyl alcohol, paraffin, and the like, and mixtures thereof.

The low melting point wax ingredient can include up to about 30 weight percent, based on the weight of wax ingredient, of a wax which has a melting point between about 180°-220° F. Illustrative of these higher melting waxes are beeswax, spermaceti, carnauba, bayberry, candelilla, montan, ozokerite, ceresin, paraffin, castor wax, Fischer-Tropsch waxes, and the like.

The antiperspirant ingredient of a present invention cosmetic stick product typically is a particulate astringent compound which has an average particle size between about 1-100 microns. Superior cosmetic stick properties are obtained if part or all of the antiperspirant ingredient is in the form of particles which have a diameter less than about one micron. Optionally, the antiperspirant ingredient can be pre-coated with a hydrophilic organic polymer to prevent interaction with the other ingredients, and to provide a sustainedrelease antiperspirant activity under application conditions.

Suitable astringent compounds include aluminum chloride, aluminum chlorohydrate, aluminum sulfocarbolate, aluminum sulfate, aluminum-zirconium chlorohydrate, zinc sulfate, zinc sulfocarbolate, and zirconium chlorohydrate. Preferred types of astringent compounds are aluminum chlorohydrates and aluminum-zirconium chlorohydrates, such as aluminum-zirconium trichlorohydrex glycine. Aluminum-zirconium tetrachlorohydrex glycine is commercially available as Rezal 36 GP Superultrafine (Reheis), and Reach AZP 908 (Reheis).

The bicarbonate deodorant ingredient of an invention cosmetic stick product is selected from alkali metal and ammonium bicarbonates, such as sodium bicarbonate, potassium bicarbonate and ammonium bicarbonate, and mixtures thereof. The bicarbonate deodorant ingredient can contain up to about 30 weight percent, based on the weight of deodorant ingredient, of an alkali metal or ammonium carbonate compound in admixture with the bicarbonate crystallites.

One important aspect of a present invention cosmetic stick product is the size and shape of the deodorant particles in the suspended phase. Another important aspect is the density of the deodorant particles relative to the density of the solid organic matrix.

BRIEF DESCRIPTION OF THE DRAWING

FIG. 1 is a scanning Electron Microscope photomicrograph illustrating particles of starchcoated sodium bicarbonate deodorant. The particle size distribution substantially is in the range between about 10–40 microns, and each particle contains an average of about 2–10 bicarbonate crystallites in the core matrix.

In another embodiment this invention provides a particulate composition which comprises particles which have an average particle size between about 5–60 microns, and an average dimensional axial ratio between about 1–25 to 1, and wherein the particles comprise a hydrophilic polymer coating having an encapsulated core content of at least two crystallites of water-soluble inorganic compound selected from alkali metal bicarbonate and ammonium bicarbonate.

The term "dimensional axial ratio" as employed herein refers to the ratio of the largest axial diameter to the other axial diameters.

The bicarbonate crystallites within the core matrix of the coated particles have an average particle size between about 1–30 microns. Preferably, at least about 90 percent of the bicarbonate crystallites have a particle size less than about 20 microns. The particle size distribution can be in the range between about 0.5–20 microns, with a smaller quantity having a particle size less than 0.5 micron.

The bicarbonate crystallites are "sand-like" and approximately spherical in configuration. Bicarbonate crystallites which are spheroidal in shape can be obtained by subjecting particulate bicarbonate to an air-jet pulverizing treatment, in which two air-jets containing entrained bicarbonate particles are impinged at high velocity. The resultant pulverized bicarbonate is recycled until the desired crystallite size distribution is obtained. The pulverized bicarbonate product can be sized into fractions as suitable for end-use purposes.

The presence of at least two crystallites of bicarbonate salt in each hydrophilic polymercoated core matrix is attributable to the micro-size of the crystallites. Some of the crystallites aggregate to form crystallite agglomerates containing between about 2–10 primary crystallites. Coating of the agglomerates yield particles which contain between about 2–10 bicarbonate crystallites in the core matrix of hydrophilic polymer-coated particles.

Similar coated particles are obtained when during a coating procedure with a hydrophilic polymer solution two or more single bicarbonate crystallites, with a liquid surface coating of hydrophilic polymer solution, make contact and coelesce into coated particles containing two or more bicarbonate crystallites in the core matrix.

The application of the hydrophilic polymer coating to the core matrix particles is accomplished by conventional means such as pan coating, fluidized coating, centrifugal fluidized coating, and the like. The coating polymer usually is dissolved in a suitable solvent such as water, methanol, ethanol, acetone, tetrahydrofuran, ethyl acetate, dimethylformamide, and the like, as appropriate for a selected polymer species. A coating polymer also can be applied in the form of an emulsion or suspension. After the coating medium is applied to the particles, the solvent medium is removed by evaporation, thereby forming a continuous film coating which encapsulates the bicarbonate crystallites.

The coating thickness on the particle surfaces typically will vary in the range between about 0.1–20 microns. The coating can consist of a single layer or multiple layers. The polymeric coating can constitute between about 5–30 weight percent of the total dry weight of the coated particles.

The hydrophilic polymer employed for coating the ingredient particles is selected from water-soluble and water-dispersible organic polymers. A mixture of polymers can be employed, and a content of between about 0.5–40 weight percent of a water-insoluble polymer, based on the coating weight, can be included.

The term "hydrophilic" as employed herein refers to an organic polymer which has a water-solubility of at least about one gram per 100 grams of water at 25° C.

Suitable hydrophilic polymers for coating particles include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, polyacrylamide, and the like. Polyvinyl acetate is illustrative of a water-insoluble polymer which can be included as an additional coating component to moderate the hydrophilicity of the coating.

The rate of particle matrix bicarbonate release from the particle core under moisture conditions can be controlled by the quantity and type of hydrophilic polymer coating on the particle surfaces.

Low molecular weight hydrophilic polymers will release the particle matrix compound at a relatively fast rate in the presence of moisture. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release particle matrix compound at a relatively fast rate. Polyethylene oxide (M.W. of 4,000,000) or partially hydrolyzed polyvinyl acetate will release at a relatively slow rate. Polyvinylpyrrolidone will release particle matrix compound at an immediate rate when in contact with underarm type of moisture.

The surfactant ingredient of an invention cosmetic stick product is selected from nonionic, cationic and anionic polymers.

Suitable surfactant polymers include cetyltrimethylammonium bromide; sodium lauryl sulfate; sodium dodecylbenzenesulfonate; ammonium lignosulfonate; condensation products of ethylene oxide with fatty alcohols, amines or alkylphenols; partial esters of fatty acids and hexitol anhydrides; polyalkylene glycol esters; and the like. Illustrative of a preferred type of surfactant polymer is polyethylene glycol (PEG) stearate, which is commercially available as PEG 600 distearate.

Optional ingredients also may be included in an invention cosmetic formulation, such as bacteriostats, fungistats, fillers, stabilizing agents, antioxidants, pigments, coloring agents, perfumes, hardeners, chelating agents, and the like.

A bacteriostat such as 2,4,4'-trichloro-2'-hydroxydiphenyl ether (Triclosan) typically is added in a quantity between about 0.08–3 weight percent, based on the weight of the cosmetic stick product.

In another embodiment this invention provides a cosmetic roll-on product consisting of a liquid organic matrix which contains about 0.5–20 weight percent of a particulate deodorant ingredient homogeneously dispersed therein, wherein the particles have an average particle size between about 5–60 microns, and an average dimensional axial ratio between about 1-2.5 to 1, and wherein the particles comprise a hydrophilic polymer coating having an encapsulated core content of at least two crystallites of water-soluble inorganic salt selected from alkali metal bicarbonate and ammonium bicarbonate.

In a further embodiment this invention provides a cosmetic roll-on product consisting of a liquid organic matrix comprising the following parts by weight of ingredients:

| | |
|---|---|
| Volatile silicone oil | 55–70 |
| liquid emollient | 3–10 | and the liquid organic matrix has homogeneously dispersed therein about 0.5–20 parts by weight of a particulate deodorant ingredient which comprises particles having an average particle size between about 5–60 microns, and an average dimensional axial ratio between about 1-2.5 to 1, and wherein the particles comprise a hydrophilic polymer matrix having an encapsulated content of at least two crystallites of water-soluble inorganic salt selected from alkali metal bicarbonate and ammonium bicarbonate.

As noted in the Background section of the specification, the relative densities of the liquid and solid phases in a cosmetic stick or roll-on product directly affects the stability and esthetics of the formulations.

Density matching of inorganic and organic phases is a significant factor in cosmetic stick and roll-on products. The present invention formulations contain a polymer-coated bicarbonate deodorant ingredient of lower density which more closely matches the density of the organic matrix of a cosmetic stick or roll-on product than does uncoated bicarbonate ingredient.

When there is density matching of organic matrix and dispersed polymer-coated bicarbonate particle phases, a cosmetic stick or roll-on product has improved dimensional stability, and better esthetic appearance and "feel" when applied to human skin.

In general, the ingredients of a formulation can be blended in any order. However, in the practice of the invention process for cosmetic stick manufacture there is advantage in utilizing a phased order of ingredient addition and blending under controlled temperature conditions. Additional advantage is obtained in the invention process if there is a short time lapse between the alkali metal bicarbonate deodorant ingredient addition step and the cosmetic stick container filling and solidifying step. Alkali metal bicarbonate can convert to alkali metal carbonate, carbon dioxide and water at elevated temperatures.

Adding the bicarbonate deodorant as the last ingredient of the blended formulation, and processing the formulation to the solid cosmetic stick formation stage within a short time period, are factors which minimize the degradation of the bicarbonate ingredient, and the undesirable formation of water and carbon dioxide vapor byproducts. The addition and mixing of the bicarbonate deodorant ingredient into the formulation, and the dispensing of the formulation into cosmetic stick containers, can be accomplished as an essentially instantaneous procedure by utilizing an integrated mixing valve nozzle device, such as the type described in U.S. Pat. Nos. 2,816,518; 3,454,198; 3,949,904; 4,318,429; 4,549,813; 5,046,538; 5,094,276; and the like.

The practice of the invention process for the production of a cosmetic stick product can be conducted in conventional equipment, and is readily adaptable to a commercial-scale manufacturing operation.

A present invention cosmetic stick product preferably has a hardness penetration value between about 4–12 millimeters, as determined by American Society For Testing Materials (ASTM) Method D5.

A present invention antiperspirant-deodorant cosmetic stick product has exceptional properties for treating or preventing perspiration and malodor associated with human underarm perspiration. A present invention cosmetic stick product can be applied effectively with safety and comfort for reduction of underarm perspiration and offensive odors.

The following Examples are further illustrative of the present invention. The components and specific ingredients are presented as being typical and various modifications can be derived in view of the foregoing disclosure within the scope of the invention.

EXAMPLE I

This Example illustrates a fluidized bed procedure for coating a particulate bicarbonate compound with a hydrophilic polymer in accordance with the present invention.

A fluidized bed vessel is utilized which is equipped with a Wurster air-suspension coater system (WARF) as described in U.S. Pat. No. 4,568,559 and U.S. Pat. No. 4,877,621.

A coating solution is prepared by dissolving polyethylene glycol (45 g, Poly-G 2000, Olin Corp.), and propylene glycol butyl ether (10 g, PPG 14, Americol) in ethanol (500 g)/water (75 g).

Sodium bicarbonate is utilized as the core matrix particles. The sodium bicarbonate (Particle Size Technology, Inc.) has an average particle size of about 5 microns, and 90 percent of the particles have a diameter less than .20 microns.

The sodium bicarbonate powder is charged into the coating chamber of the coater system.

Compressed air is introduced into the coating chamber, and the polymeric coating solution is sprayed on the air-suspended bicarbonate core matrix particles, until the coating weight is about 30% of the total dry weight of the coated particles.

The procedure is repeated, except that Hydroxypropylmethylcellulose (Methocel 60 HG, Dow Chemical Co.) is employed as the hydrophilic polymer.

The procedure is repeated, except that maltodextrin (Lodex 10; Durkee Foods) or amylodextrin is employed as the water-soluble polymer, and 0.5 g of a surfactant is included in the solution (polyoxyethylenesorbitan monolaurate; Tween 20; ICI Americas, Inc.)

The coated particles consist of a hydrophilic polymer coating on an inner core of 2-10 crystallites of sodium bicarbonate. The coated particles have an average particle size of about 35 microns.

EXAMPLE II

This Example illustrates a procedure for the preparation of an antiperspirant-deodorant cosmetic stick product in accordance with the present invention.

A stainless steel tank is provided which is equipped with turbine agitation.

Silicone oil DC 245 (400 lbs, Dow Corning) and Dow DC 200 (37.50 lbs, Dow Corning) are charged to the mixing tank. Agitation (55-65 RPM) is initiated, and heating the liquid medium to 176° F. is commenced.

During the heating period, the following ingredients are added to the stirred liquid medium:

|  | lbs. |
|---|---|
| Lanette 18 DEO[1] | 175.00 |
| Castorwax MP-80[2] | 31.25 |
| ICI G-2162[3] | 6.25 |

[1] Stearyl alcohol; Henkel.
[2] Hydrogenated castor oil; RTD.
[3] PEG 25 PG stearate; ICI.

The mixture is stirred at 176° F. for about 30 minutes until the ingredients are melted and the liquid medium is homogeneous. The stirring speed is reduced to about 35 RPM, then Cyprus Supra A Talc 1625 (18.75 lbs, Cyprus) and Reach AZP 908 aluminum zirconium tetrachlorohydrex glycine (312.50 lbs, Reheis) are added. The temperature is maintained at 176° F. for about 40 minutes until the fluid medium is uniform, and then the temperature is lowered to 154° F.

Polymer-coated sodium bicarbonate (140 lbs.) and Sobica F41 fragrance (6.25 lbs, Takasago) respectively are added with stirring to Silicone oil DC 245 (200 lbs, Dow Corning) in a second mixing tank at a temperature of 154° F. to form a homogeneous suspension medium. The sodium bicarbonate particles are pre-coated with amylodextrin as described in Example I.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 7 (ASTM Method D5).

EXAMPLE III

This Example illustrates a pilot-plant procedure for the preparation of an antiperspirant-deodorant cosmetic stick product in accordance with the present invention.

A stainless steel tank is provided which is equipped with turbine agitation.

DC 245 silicone (1440 lbs.) is charged to the mixing tank. Stirring is commenced, and Dow DC 200 (50 cst., 50 lbs.) and ICI G-2162 (15 lbs) are added. The mixture is heated to 178° F., and the temperature is maintained during ingredient addition.

Lanette 18 DEO (420 lbs.), Castorwax MP-80 (75 lbs.), Cyprus Supra A Talc 1625 (45 lbs.), Reach AZP 908 (750 lbs), and encapsulated particulate sodium bicarbonate (150 lbs, 30% weight percent starch coating) are added successively.

The rate of stirring is reduced to allow de-aeration of the liquid blend, and the blend is cooled slowly to 150° F. Sobica F41 (15 lbs.) is added, and slow stirring is continued until the formulation is homogeneous.

The formulation is distributed into cosmetic stick containers, and cooled in the manner described in Example II.

EXAMPLE IV

This Example illustrates the preparation of an antiperspirant-deodorant roll-on product in accordance with the present invention.

A roll-on formulation is prepared by blending the following proportions of ingredients:

|  | lbs. |
|---|---|
| Silicone oil DC 245 | 60.90 |
| Quaternium-18 hectorite clay (Rheox) | 10.00 |
| Reach AZP 908 | 23.00 |
| Encapsulated sodium bicarbonate | 5.00 |
| Cab-o-Sil fumed silica (Cabot) | 0.60 |
| Sobica F41 | 0.50 |

The roll-on formulation exhibits excellent dimensional stability when packaged and maintained under storage conditions for six months.

What is claimed is:

1. A cosmetic stick product consisting of a solid organic matrix which contains about 0.5-20 weight percent of a particulate deodorant ingredient homogeneously dispersed therein, wherein the particles have an average particle size between about 5-60 microns, and an average dimensional axial ratio between about 1-2.5 to 1, and wherein the particles comprise a water-soluble or water-dispersible hydrophilic polymer surface coating having an encapsulated core content of at least two crystallites of water-soluble inorganic compound selected from alkali metal bicarbonate and ammonium bicarbonate.

2. A cosmetic stick product consisting to a solid organic matrix comprising the following parts by weight of ingredients:

|  |  |
|---|---|
| volatile silicone oil | 10-55 |
| liquid emollient | 1-35 |

| | |
|---|---|
| low melting point wax | 12-30 | and the solid organic matrix has homogeneously dispersed therein about 0.5-20 parts by weight of a particulate deodorant ingredient which comprises particles having an average particle size between about 5-60 microns, and an average dimensional axial ratio between about 1-2.5 to 1, and wherein the particles comprise a water-soluble or water-dispersible hydrophilic polymer surface coating having an encapsulated core content of at least two crystallites of water-soluble inorganic compound selected from alkali metal bicarbonate and ammonium bicarbonate.

3. A cosmetic stick product in accordance with claim 2 wherein the volatile silicone oil ingredient comprises a cyclic or linear polydimethylisiloxane containing 3-9 silicon atoms.

4. A cosmetic stick product in accordance with claim 2 wherein the liquid emollient ingredient is a water-insoluble organic acid, ester or ether compound.

5. A cosmetic stick product in accordance with claim 2 wherein the wax ingredient is selected from $C_8$-$C_{30}$ alcohol, acid, ester and amide compounds.

6. A cosmetic stick product in accordance with claim 2 wherein the coated bicarbonate deodorant ingredient is sodium, potassium or ammonium bicarbonate or mixtures thereof.

7. A cosmetic stick product in accordance with claim 2 wherein the hydrophilic polymer surface coating of the particulate deodorant ingredient is a polysaccharide derivative.

8. A cosmetic stick product in accordance with claim 2 wherein the hydrophilic polymer surface coating of the particulate deodorant ingredient is a hydrocolloid gum.

9. A cosmetic stick product in accordance with claim 2 wherein the hydrophilic polymer surface coating of the particulate deodorant ingredient is a water-soluble starch derivative.

10. A cosmetic stick product in accordance with claim 2 wherein the hydrophilic polymer surface coating of the particulate deodorant ingredient is maltodextrin or amylodextrin or a mixture thereof.

11. A cosmetic stick product in accordance with claim 2 wherein the matrix further comprises between about 0.08-3 weight percent of a bacteriostat as an additional ingredient, based on the weight of cosmetic stick product.

12. An antiperspirant-deodorant cosmetic stick product comprising the following weight percent of ingredients:

| | |
|---|---|
| volatile silicone oil | 25-50 |
| liquid emollient | 2-20 |
| low melting point wax | 15-20 |
| antiperspirant | 20-28 |
| particulate bicarbonate deodorant | 0.1-25 |
| surfactant | 1-3 | wherein the particulate deodorant ingredient comprises particles having an average particle size between about 5-60 microns, and an average dimensional axial ratio between about 1.2-5 to 1, and wherein the particles comprise a water-soluble or water-dispersible hydrophilic polymer surface coating having an encapsulated core content of at least two crystallites of water-soluble inorganic salt selected from alkali metal bicarbonate and ammomium bicarbonte.

13. An antiperspirant-deodorant cosmetic stick product in accordance with claim 12 wherein the antiperspirant ingredient is selected from astringent aluminum and zirconium compounds, and complexes or mixtures thereof.

14. An antiperspirant-deodorant cosmetic stick product in accordance with claim 12 wherein the antiperspirant ingredient is an aluminum-zirconium tetrachlorohydrate compound.

15. An antiperspirant-deodorant cosmetic stick product in accordance with claim 12 wherein the deodorant ingredient is sodium, potassium or ammonium bicarbonate or mixtures thereof.

16. An antiperspirant-deodorant cosmetic stick product in accordance with claim 12 wherein the surfactant ingredient is selected from nonionic, cationic and anionic polymers.

17. An antiperspirant-deodorant cosmetic stick product in accordance with claim 12 wherein the surfactant ingredient is polyalkylene glycol diester.

18. A cosmetic roll-on product consisting of a liquid organic matrix which contains about 0.5-20 weight percent of a particulate deodorant ingredient homogeneously dispersed therein wherein the particles comprise a water-soluble or water-dispersible hydrophilic polymer surface coating having an encapsulated core content of at least two crystallites of water-soluble inorganic compounds selected from alkali metal bicarbonate and ammonium bicarbonate.

19. A cosmetic roll-on product consisting of a liquid organic matrix comprising the following part by weight of ingredients:

| | |
|---|---|
| volatile silicone oil | 55-70 |
| liquid emollient | 3-10 | and the liquid organic matrix has homogeneously dispersed therein about 0.5-20 parts by weight of a particulate deodorant ingredient which comprises particles having an average particle size between about 5-60 microns, and an average dimensional axial ratio between about 1-2.5 to 1, and wherein the particles comprise a water-soluble or water-dispersible hydrophilic polymer surface coating having an encapsulated core content of at least two crystallites of water-soluble inorganic compounds selected from alkali metal bicarbonate and ammonium bicarbonate.

20. A cosmetic roll-on product in accordance with claim 19 wherein the deodorant ingredient is sodium, potassium or ammonium bicarbonate or mixtures thereof.

21. A cosmetic roll-on product in accordance with claim 19 which contains between about 15-25 parts by weight of an antiperspirant compound as an additional ingredient.

* * * * *